(12) United States Patent
Allegretti et al.

(10) Patent No.: US 7,674,806 B2
(45) Date of Patent: Mar. 9, 2010

(54) AMIDINES AND DERIVATIVES THEREOF AND PHARMACEUTICAL COMPOSITIONS CONTAINING THEM

(76) Inventors: Marcello Allegretti, Via Campo di Pile, I-67100 L'Aquila (IT); Maria Candida Cesta, Via Campo di Pile, I-67100 L'Aquila (IT); Giuseppe Nano, Via Campo di Pile, I-67100 L'Aquila (IT); Riccardo Bertini, Via Campo di Pile, I-67100 L'Aquila (IT); Cinzia Bizzarri, Via Campo di Pile, I-67100 L'Aquila (IT); Francesco Colotta, Via Campo di Pile, I-67100 L'Aquila (IT)

( * ) Notice: Subject to any disclaimer, the term of this patent is extended or adjusted under 35 U.S.C. 154(b) by 551 days.

(21) Appl. No.: 10/568,760

(22) PCT Filed: Sep. 16, 2004

(86) PCT No.: PCT/EP2004/052201

§ 371 (c)(1),
(2), (4) Date: Jan. 5, 2007

(87) PCT Pub. No.: WO2005/028425

PCT Pub. Date: Mar. 31, 2005

(65) Prior Publication Data

US 2007/0155717 A1    Jul. 5, 2007

(30) Foreign Application Priority Data

Sep. 25, 2003    (EP) ................... 03103557

(51) Int. Cl.
*C07D 417/02*    (2006.01)
*C07D 413/02*    (2006.01)
*A61K 31/553*    (2006.01)
*A61K 31/541*    (2006.01)
*A61K 31/5377*    (2006.01)

(52) U.S. Cl. ................ 514/331; 546/229
(58) Field of Classification Search ............ 546/229; 514/331
See application file for complete search history.

(56) References Cited

U.S. PATENT DOCUMENTS 2,919,274 A    12/1959    Faust et al.

FOREIGN PATENT DOCUMENTS

| CA | 2 372 673 A1 | 11/2001 |
|---|---|---|
| DE | 24 39 299 A1 | 3/1975 |
| EP | 1 170 288 A | 1/2002 |
| WO | WO-01/58852 A | 8/2001 |

OTHER PUBLICATIONS

Abstract of Delaby et al. Compt. rend, (1958), 346, 2905-6.*
Database Caplus Online, Nardi, D et al., Farmaco, Edizione Scientifica, 34 (9), 789-801 Coden: Frpsax; Issn: 0430-0920, 1979.
Database Beilstein, J. Chem. Soc. Chem. Commun., 1974, pp. 706-708.
Database Caplus, European Journal of Medicinal Chemistry, 16 (2), 175-9 Coden: Ejmca5; Issn: 0009-4374, 1981.
Database Caplus, Delaby, Raymond et al., Bulletin De La Societe Chimique De France 2067 Coden: Bscfas; Issn: 0037-8968, 1961.
Database Beilstein, C.R. Hebd. Seances Acad. Sci., vol. 246, 1958, pp. 2906.
Database Beilstein Bull. Soc. Chim. Fr., 1961, pp. 1820-1821.
Database Chemcats, Interchim Intermediates, Sep. 17, 2004, Interchim, Montlucon, FR.
Database Chemcats, Salor, Aug. 20, 2004, Aldrich Chemical Company, Inc, Milwaukee, USA.

* cited by examiner

*Primary Examiner*—Kahsay T Habte
(74) *Attorney, Agent, or Firm*—Birch, Stewart, Kolasch & Birch, LLP

(57) ABSTRACT

Amidines and derivatives thereof of formula (I) are described. The process for their preparation and pharmaceutical compositions thereof are also described. The amidines of the invention are useful in the inhibition of chemotaxis of neutrophils induced by IL-8. The compounds of the invention are used in the treatement of psoriasis, ulcerative colitis, melanoma, chronic obstructive pulmonary disease (COPD), bullous pemphigo, rheumatoid arthritis, idiopathic fibrosis, glomerulonephritis and in the prevention and treatment of damages caused by ischemia and reperfusion.

7 Claims, No Drawings

AMIDINES AND DERIVATIVES THEREOF AND PHARMACEUTICAL COMPOSITIONS CONTAINING THEM

The present application is a National Stage entry of PCT/EP2004/052201 filed on Sep. 16 2004. Priority is also claimed to European patent application 03103557.9 filed Sep. 25, 2003 under 35 U.S.C. §119.

BRIEF DESCRIPTION OF THE INVENTION

The present invention relates to amidines and derivatives thereof and to pharmaceutical compositions containing them, which are used in the prevention and treatment of tissue damage due to the exacerbated recruitment of polymorphonucleate neutrophils (PMN leukocytes) at inflammation sites.

STATE OF THE ART

Particular blood cells (macrophages, granulocytes, neutrophils, polymorphonucleated) respond to a chemical stimulus (when stimulated by substances called chemokines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including Interleukin-8 (IL-8, also referred to as CXCL8). Interleukin-8 is an endogenous chemotactic factor produced by most nucleated cells such as fibroblasts and macrophages.

In some pathological conditions, marked by exacerbated recruitment of neutrophils, a more severe tissue damage at the site is associated with the infiltration of neutrophilic cells. Recently, the role of neutrophilic activation in the determination of damage associated with post ischemia reperfusion and pulmonary hyperoxia was widely demonstrated.

The biological activity of IL-8 is mediated by the interaction of the interleukin with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995). Selective ligand are known which can distinguish between CXCR1 and CXCR2: GRO-α is an example of a CXCR2 selective chemotactic factor.

Although CXCR1 activation is known to play a crucial role in IL-8-mediated chemotaxis, it has been recently supposed that CXCR2 activation could play a pathophysiological role in cronic inflammatory diseases such as psoriasis. In fact, the pathophysiological role of IL-8 in psoriasis is also supported by the effects of IL-8 on keratinocyte functions.

Indeed, IL-8 has been shown to be a potent stimulator of epidermal cell proliferation as well as angiogenesis, both important aspects of psoriatic pathogenesis (A. Tuschil et al. J Invest Dermatol, 99, 294, 1992; Koch A E et al, Science, 258, 1798, 1992).

In addition, there is accumulating evidence that the pathophysiological role of IL-8 in melanoma progression and metastasis could be mediated by CXCR2 activation (L. R. Bryan et al., Am J Surg, 174, 507, 1997).

Potential pathogenic role of IL-8 in pulmonary diseases (lung injury, acute respiratory distress syndrome, asthma, chronic lung inflammation, and cystic fibrosis) and, specifically, in the pathogenesis of COPD (chronic obstructive pulmonary disease) through the CXCR2 receptor pathway has been widely described (D. W P Hay and H. M. Sarau., Current Opinion in Pharmacology 2001, 1:242-247).

Studies on the contribution of single (S) and (R) enantiomers of ketoprofen to the anti-inflammatory activity of the racemate and on their role in the modulation of the chemokine have demonstrated (P. Ghezzi et al., J. Exp. Pharm. Ther., 287, 969, 1998) that the two enantiomers and their salts with chiral and non-chiral organic bases can inhibit in a dose-dependent way the chemotaxis and increase in intracellular concentration of $Ca^{2+}$ ions induced by IL-8 on human PMN leukocytes (patent application U.S. Pat. No. 6,069,172). It has been subsequently demonstrated (C. Bizzarri et al., Biochem. Pharmacol. 61, 1429, 2001) that Ketoprofen shares the property to inhibit the IL-8 biological activity with other molecules belonging to the class of non-steroidal anti-inflammatory (NSAIDs) such as flurbiprofen, ibuprofen and indomethacin. The cyclo-oxygenase enzyme (COX) inhibition activity typical of NSAIDs limits the therapeutical application of these compounds in the context of the treatment of neutrophil-dependent pathological states and inflammatory conditions such as psoriasis, idiopathic pulmonary fibrosis, acute respiratory failure, damages from reperfusion and glomerulonephritis. The inhibition of prostaglandin synthesis deriving from the action on cyclo-oxygenase enzymes involves the increase of the cytokine production which, like TNF-α, play a role in amplifying the undesired pro-inflammatory effects of neutrophils.

Novel classes of potent and selective inhibitors of IL-8 biological activities suitable for "in vivo" administration. R-2-arylpropionic acid amides and N-acylsulfonamides have been described as effective inhibitors of IL-8 induced neutrophils chemotaxis and degranulation (WO 01/58852; WO 00/24710). Furthermore, novel R and S-2-phenylpropionic acids have been recently described as potent IL-8 inhibitors completely lacking the undesired COX inhibitory effect has been described in WO 03/043625.

DETAILED DESCRIPTION OF THE INVENTION

We have now found that a novel class of amidines and derivatives thereof show the ability to effectively inhibit IL-8 induced neutrophils chemotaxis and degranulation.

The present invention thus provides amidines and derivatives thereof of formula (I):

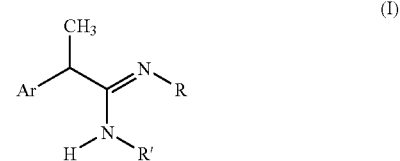

(I)

and pharmaceutically acceptable salts thereof, wherein Ar is a phenyl group non-substituted or substituted by one or more groups independently selected from halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halogen-$C_1$-$C_3$-alkyl, halogen $C_1$-$C_3$-alkoxy, benzoyl or a substituted or unsubstituted 5-6 membered heteroaryl ring selected from pyridine, pyrrole, thiophene, furane, indole.

R' is selected from
H, $C_1$-$C_5$-alkyl, phenyl, $C_1$-$C_5$-phenylalkyl, $C_1$-$C_5$-cycloalkyl, $C_1$-$C_5$-alkenyl, $C_1$-$C_5$-alkoxy;
a residue of formula —(CH2)n-NRaRb wherein n is an integer from 0 to 5 and each Ra and Rb, which may be the same or different, are $C_1$-$C_6$-alkyl, $C_1$-$C_6$-alkenyl or, alternatively, Ra and Rb, together with the nitrogen atom to which they are bound, form a heterocycle from 3 to 7 members of formula (II)

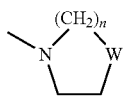

(II)

wherein W represents a single bond, O, S, N-Rc, Rc being H, $C_1$-$C_6$-alkyl or $C_1$-$C_6$-alkylphenyl, n is an integer from 0 to 4.

R is H, $CH_3$, $CH_2CH_3$.

R and R' can alternatively, form a heterocycle from 5 to 7 members of formula (III)

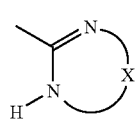

(III)

where X represents a residue —O($CH_2$)n- wherein n is an integer from 1 to 3, or a residue —($CH_2$)n- wherein n is an integer from 2 to 4, or the ethylene residue —CH=CH—.

When R' is $C_1$-$C_5$ alkyl, such alkyl group can be optionally interrupted by an heteroatom such as oxygen or sulfur. For example, R' can be a residue of formula —$CH_2$—$CH_2$—Z—$CH_2$—$CH_2$OR" wherein R" is H or $C_1$-$C_5$-alkyl.

Compounds of formula (I) are chiral compounds and the invention provides both the racemic and the single (R) and (S) enantiomers.

It is a further object of the present invention compounds of formula (I) as defined above for use as medicaments. In particular, the invention provides the compounds of formula (I) for use as inhibitors of IL-8 induced human PMNs chemotaxis.

When Ar is a phenyl group preferred phenyl groups are substituted by:
 a group in the 3 (meta) position selected from a linear or branched $C_1$-$C_5$ alkyl, $C_2$-$C_5$-alkenyl or $C_2$-$C_5$-alkynyl group, substituted or not-substituted phenyl, linear or branched $C_1$-$C_5$ hydroxyalkyl, $C_2$-$C_5$-acyl, substituted or not-substituted benzoyl;
 a group in the 4 (para) position selected from $C_1$-$C_5$ alkyl, $C_2$-$C_5$-alkenyl or $C_2$-$C_5$-alkynyl group, $C_3$-$C_6$-cycloalkyl, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, 2-furyl; 3-tetrahydrofuryl; 2 thiophenyl; 2-tetrahydrothiophenyl groups or a $C_1$-$C_8$ (alkanoyl, cycloalkanoyl, arylalkanoyl)-$C_1$-$C_5$-alkylamino, e.g. acetyl-N-methyl-amino, pivaloyl-N-ethyl-amino group;

When Ar is a heteroaromatic ring preferred heteroaromatic rings are
 pyrrole, thiophene, furane.
 Preferred R' groups are
 H, $C_1$-$C_5$ alkyl, $C_1$-$C_5$-phenylalkyl;
 a residue of formula —(CH2)n-NRaRb wherein n is an integer from 2 to 3, more preferably 3, and the group NRaRb is N,N-dimethylamine, N,N-diethylamine, 1-piperidyl, 4-morpholyl, 1-pyrrolidyl, 1-piperazinyl, 1-(4-methyl)piperazinyl;

More preferably the group NRaRb is N,N-dimethylamine or 1-piperidyl.

Preferred R group is H;

when R and R' form a heterocycle of formula (III) X preferably represents a residue —O($CH_2$)n- wherein n is the integer 1 or 2, or a residue —($CH_2$)$_2$.

Particularly preferred compounds of the invention are:
(R,S) (2-(4-isobutylphenyl)propionamidine hydrochloride
(+) (2-(4-isobutylphenyl)propionamidine hydrochloride
(−) (2-(4-isobutylphenyl)propionamidine hydrochloride
(R,S) 2-(3-benzoylphenyl)propionamidine hydrochloride
(R,S) 2-[(3-fluoro-4-phenyl)phenyl]propionamidine hydrochloride
(R,S) 2-(4-trifluoromethanesulfonyloxyphenyl)propionamidine hydrochloride
(R,S) 2-(5-benzoyl-2-thiophene)propionamidine hydrochloride
(R,S) 2-(4-isobutylphenyl)-N-[3"-(N'-piperidino)propyl] propionamidine dihydrochloride
(R,S) 2-(4-isobutylphenyl)-N-methyl-propionamidine hydrochloride
(R,S) 2-(3-benzoylphenyl)- N-[3-(N,N-dimethylamino)propyl]propionamidine hydrochloride
(R,S) 2-(4-isobutylphenyl)propionamidine acetate salt
(R,S) 2-(4-isobutylphenyl)-N-[3-(N,N-dimethylamino)propyl] propionamidine
(R,S) 2-(4-isobutylphenyl)-N-benzyl propionamidine
(R,S) 3-[1-(4-isobutylphenyl)ethyl]-5,6-dihydro-2H-1,2,4-oxadiazine
(R,S) 2-[1-(4-isobutylphenyl)ethyl]-4,5-dihydro-2H-1,3, imidazole.

The compounds of the invention are potent and selective inhibitors of the human PMNs chemotaxis induced by IL-8.

The compounds of the invention of formula (I) are generally isolated in the form of their addition salts with both organic and inorganic pharmaceutically acceptable acids.

Examples of such acids are selected from hydrochloric acid, sulfuric acid, phosphoric acid, metansolfonic acid, fumaric acid, citric acid.

Compounds of formula (I) are obtained by treatment of corresponding nitrile derivatives of formula (IV),

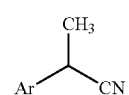

(IV)

wherein Ar has the same meaning as defined above, in a MeOH/HCl solution and subsequent reaction of the imidate intermediates with the amines of formula NHR, wherein R has the same meaning as defined above, in a dry organic solvent such as dichloromethane;

Compounds of formula (I) wherein R and R' groups form an heterocycle of formula (III) are obtained by direct cyclization of amides of formula (V),

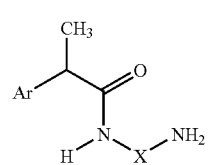

(V)

wherein X has the same meaning as defined above, with a suitable catalyst such as Al(CH$_3$)$_3$.

Alternatively, compounds of formula (I), wherein R and R' groups form an heterocycle of formula (III) are obtained by direct reaction of amidines of formula (I) wherein R is H and R' is H or OH, with a reagent of formula L-K-L', in the presence of a base, wherein L and L' are common leaving groups such as halogens, mesylate, etc, and, when R and R' are both H, K represents a residue —(CH$_2$)n-, wherein n is an integer from 2 to 4; when R' is OH and R is H, K represents a residue —(CH$_2$)n-, wherein n is an integer from 1 to 3.

The compounds of the invention of formula (I) were evaluated in vitro for their ability to inhibit chemotaxis of polymorphonucleate leukocytes (hereinafter referred to as PMNs) and monocytes induced by the fractions of IL-8 and GRO-α. For this purpose, in order to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant IL-8 (Pepro Tech) was used as stimulating agents in the chemotaxis experiments, giving practically identical results: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-9}$ M, for the chemotaxis assays.

During the chemotaxis assay (according to W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula I to inhibit IL-8-induced chemotaxis of human monocytes was carried out according to the method disclosed by Van Damme J. et al. (Eur. J. Immunol., 19, 2367, 1989).

Particularly preferred compounds of the invention are compounds of Formula I in which Ar groups are 3'-benzoylphenyl, 3'-(4-chloro-benzoyl)-phenyl, 3'-(4-methyl-benzoyl)-phenyl, 3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'acetylaminophenyl, 4'propionylamino-phenyl, 4'-benzoylamino-phenyl, which show the additional property to effectively inhibit the GRO' induced PMN chemotaxis; this activity allows the therapeutic use of these compounds in IL-8 related pathologies where the CXCR2 pathway is involved specifically or in conjunction with the CXCR1 signalling.

The dual inhibitors of the IL-8 and GRO-α induced biological activities are strongly preferred in view of the therapeutical applications of interest, but the described compounds selectively acting on CXCR1 IL-8 receptor or CXCR2 GRO-α/IL-8 receptor can find useful therapeutic applications in the management of specific pathologies as below described.

The compounds of formula I, evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In the most of the cases, the compounds of formula (I) do not interfere with the production of PGE$_2$ induced in murine macrophages by lipopolysaccharides stimulation (LPS, 1 μg/mL) at a concentration ranging between $10^{-5}$ and $10^{-7}$ M. Inhibition of the production of PGE$_2$ which may be recorded, is mostly at the limit of statistical significance, and more often is below 15-20% of the basal value. The reduced effectiveness in the inhibition of the CO constitutes an advantage for the therapeutic application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

In view of the experimental evidence discussed above and of the role performed by Interleukin-8 (IL-8) and congenetics thereof in the processes that involve the activation and the infiltration of neutrophils, the compounds of the invention are particularly useful in the treatment of a disease such as psoriasis (R. J. Nicholoff et al., Am. J. Pathol., 138, 129, 1991). Further diseases which can be treated with the compounds of the present invention are intestinal chronic inflammatory pathologies such as ulcerative colitis (Y. R. Mahida et al., Clin. Sci., 82, 273, 1992) and melanoma, chronic obstructive pulmonary disease (COPD), bullous pemphigo, rheumatoid arthritis (M. Selz et al., J. Clin. Invest., 87, 463, 1981), idiopathic fibrosis (E. J. Miller, previously cited, and P. C. Carrét al., J. Clin. Invest., 88, 1882, 1991), glomerulonephritis (T. Wada et al., J. Exp. Med., 180, 1135, 1994) and in the prevention and treatment of damages caused by ischemia and reperfusion.

Inhibitors of CXCR1 and CXCR2 activation find useful applications, as above detailed, particularly in treatment of chronic inflammatory pathologies (e.g. psoriasis) in which the activation of both IL-8 receptors is supposed to play a crucial pathophysiological role in the development of the disease.

In fact, activation of CXCR1 is known to be essential in IL-8-mediated PMN chemotaxis (Hammond M et al, J Immunol, 155, 1428, 1995). On the other hand, activation of CXCR2 activation is supposed to be essential in IL-8-mediated epidermal cell proliferation and angiogenesis of psoriatic patients (Kulke R et al., J Invest Dermatol, 110, 90, 1998).

In addition, CXCR2 selective antagonists find particularly useful therapeutic applications in the management of important pulmonary diseases like chronic obstructive pulmonary disease COPD (D. WP Hay and H. M. Sarau., Current Opinion in Pharmacology 2001, 1:242-247).

It is therefore a further object of the present invention to provide compounds for use in the treatment of psoriasis, ulcerative colitis, melanoma, chronic obstructive pulmonary disease (COPD), bullous pemphigo, rheumatoid arthritis, idiopathic fibrosis, glomerulonephritis and in the prevention and treatment of damages caused by ischemia and reperfusion, as well as the use of such compounds in the preparation of a medicament for the treatment of diseases as described above. Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the amidines of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined on the basis of relevant circumstances including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermaldermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can be found in the incorporated materials in the Remington's Handbook as above.

The present invention shall be illustrated by means of the following examples which are not construed to be viewed as limiting the scope of the invention.

Abbreviations: THF: tetrahydrofuran; DMF: dimethylformamide; AcOEt: ethyl acetate.

EXPERIMENTAL PROCEDURES

Example 1

Starting from the procedure described in Granik, *Russ. Chem. Rev.*, 52, 377-393 (1983), the following unsubstituted amidines can be prepared:

1a (R,S) (2-(4-Isobutylphenyl)Propionamide Hydrochloride 2-(4-isobutylphenyl)propionitrile 4-isobutyl-α-methylphenylacetamide (2 g; 9.7 mmol), prepared according the procedure described in WO 00/24710, is dissolved in a solution (2:1) toluene/trichloromethane (30 mL). 20% in toluene phosgene (15.5 mL, 30 mmol) is added and the resulting mixture is left stirring 12 h under inert atmosphere until the complete disappearance of the starting reagent. After solvents evaporation under reduced pressure, the crude is dissolved in ethyl acetate (20 mL), the organic phase is washed with a saturated solution of NaHCO$_3$ (2×20 mL) and with a saturated solution of NaCl (2×15 mL), dried over Na$_2$SO$_4$ and evaporated under vacuum to give 2-(4-isobutylphenyl)propionitrile as colourless oil (1.45 g; 7.76 mmol). Yield 80%. $^1$H-NMR (CDCl$_3$): δ 7.42 (d, 2H, J=7 Hz); 7.28 (d, 2H, J=7 Hz); 4.05 (q, 1H, J=8 Hz); 2.65 (d, 2H, J=8 Hz); 1.95 (m, 1H); 1.80 (d, 3H, J=8 Hz); 1.05 (d, 6H, J=8 Hz).

A solution of 2-(4-isobutylphenyl)propionitrile (0.2 g; 1.07 mmol) in a (1:1) diethyl ether/methyl alcohol mixture (20 mL) is cooled at T=0-5° C. and gaseous HCl is bubbled into the solution for 1 h. Then the temperature is left to arise to r.t. and the mixture stirred overnight. After solvent evaporation under reduced pressure, the crude is dissolved in methyl alcohol (10 mL) and cooled at T=0-5° C. Ammonia is bubbled into for 1 h and the resulting mixture is left stirring overnight at r.t. After solvent evaporation under reduced pressure, the crude is suspended in diethyl ether (15 mL) and left stirring at r.t. for 2 h. The 2-(4-isobutylphenyl)propionamide hydrochloride (I) is isolated by filtration in vacuo as white solid (0.193 g; 0.80 mmol). Yield 75%. $^1$H-NMR (DMSO-d$_6$): δ 8.80-8.50 (bs, NH$_3^+$Cl$^-$); 7.40 (d, 2H, J=7 Hz); 7.15 (d, 2H, J=7 Hz); 3.98 (q, 1H, J=8 Hz); 2.42 (d, 2H, J=8 Hz); 1.90 (m, 1H); 1.57 (d, 3H, J=8 Hz); 0.88 (d, 6H, J=8 Hz).

According to the above described method and using the suitable carboxylic acid, the following compounds have been prepared:

1b (R,S) 2-(3-Benzoylphenyl)Propionamidine Hydrochloride from 2-(3'-benzoylphenyl)propionitrile, prepared following the procedure above described, and the corresponding α-methylphenylacetamide. The general preparation in described in WO/0158852.

Yield 70%. m.p. 110-113° C. $^1$H-NMR (DMSO-d$_6$): δ 7.86 (s, 1H); 7.80-7.50 (m, 8H+NH$_2^+$+NH$_2$); 4.13 (q, 1H, J=7 Hz); 1.60 (d, 3H, J=7 Hz).

1c (R,S) 2-[(3-Fluoro-4-Phenyl)Phenyl]Propionamidine Hydrochloride

From 2-(3-fluoro-4-phenyl)propionitrile, prepared following the procedure above described, and the corresponding α-methylphenylacetamide. The general preparation in described in WO/0158852.

Yield 53%. m.p. 143-145° C. $^1$H-NMR (DMSO-d$_6$): δ 9.18 (bs, NH$_2^+$Cl$^-$); 8.85 (bs, NH$_2$); 7.67-7.30 (m, 8H); 4.15 (q, 1H, J=7 Hz); 1.62 (d, 3H, J=7 Hz).

1d (R,S) 2-(4-Trifluoromethanesulfonyloxyphenyl)Propionamidine Hydrochloride

From 2-(4'-trifluoromethanesulfonyloxyphenyl)propionitrile, prepared following the procedure above described, and the corresponding α-methylphenylacetamide.

Yield 68%. $^1$H-NMR (DMSO-d$_6$): δ 7.47 (d, 2H, J=8 Hz); 7.25 (d, 2H, J=8 Hz); 6.55 (bs, NH$_2$+NH$_2^+$Cl$^-$); 3.92 (q, 1H, J=7 Hz); 1.56 (d, 3H, J=7 Hz).

1e (R,S) 2-(5-Benzoyl-2-Thiophene)Propionamidine Hydrochloride

From 2-(5-benzoyl-2-thiophene)propionitrile, prepared following the procedure above described, and the corresponding propionamide.

Yield 60% $^1$H-NMR (DMSO-d$_6$): δ 7.9 (d, 2H, J=8 Hz); 7.7-7.4 (m, 4H); 7.0 (d, 1H, J=8 Hz); 6.55 (bs, NH$_2$+NH$_2^+$Cl$^-$); 3.9 (q, 1H, J=7 Hz); 1.56 (d, 3H, J=7 Hz).

Optical Resolution of (R,S) (2-(4-Isobutylphenyl)Propionamidine

Single (+) and (−) enantiomers of (2-(4-isobutylphenyl) propionamidine have been obtained by optical resolution starting from (R,S) (2-(4-isobutylphenyl)propionamidine hydrochloride. The free base has been obtained by treatment of the hydrochloride salt with strongly basic AMBERLITE IRA-910 resin.

Corresponding (L) and (D) tartrate salts have been prepared by treatment of (R,S) (2-(4-isobutylphenyl)propionamidine with (L) and (D) tartrate in methanol. Optically pure (+) and (−) (2-(4-isobutylphenyl)propionamidine isomers have been obtained by sequential cristallization steps of the tartrate salts from isopropanol (or acetone) solution.

The free bases have been obtained by treatment of the tartrate salt with strongly basic AMBERLITE IRA-910 resin.

1f (+) (2-(4-Isobutylphenyl)Propionamidine
[α]$_D$=+28.1 (c=0.5, MeOH)

1g (−) (2-(4-Isobutylphenyl)Propionamidine
[α]$_D$=−28.0 (c=0.5, MeOH)

Example 2

2a (R,S) 2-(4-Isobutylphenyl)-N-[3-(N-Piperidino)Propyl] Propionamidine Dihydrochloride A solution of 2-(4-isobutylphenyl)propionitrile (0.15 g; 0.80 mmol) in a (1:1) diethyl ether/methyl alcohol mixture (10 mL) is cooled at T=0-5° C. and gaseous HCl is bubbled into the solution for 1 h. Then the temperature is left to arise to r.t. and the mixture stirred overnight. After solvent evaporation under reduced pressure, the crude is dissolved in methyl alcohol (10 mL) and cooled at T=0-5° C. A solution of 3-piperidinopropylamine (0.15 g; 0.96 mmol) in methyl alcohol (5 mL) is added dropwise and the resulting mixture is left under stirring overnight at r.t. After solvent evaporation under reduced pressure, the crude oil is suspended in 2N HCl (solution pH=2) and the product is extracted with dichloromethane (3×15 mL). The combined organic extracts are washed back with a saturated solution of NaCl (2×15 mL), dried over Na$_2$SO$_4$ and evaporated under vacuum to give 2-(4'-isobutylphenyl)-N-[3-(N-piperidino)propyl]propionamidine dihydrochloride as glassy solid (0.193 g; 0.48 mmol). Yield 60%. $^1$H-NMR (CDCl$_3$): δ 10.88 (bs, NH$^+$Cl$^-$); 10.22 (bs, NH$^+$Cl$^-$); 9.82 (bs, NH$^+$Cl$^-$); 7.64 (bs, NH); 7.41 (d, 2H, J=8 Hz); 7.15 (d, 2H, J=8 Hz); 4.39 (q, 1H, J=8 Hz); 3.78 (m, 2H); 3.45 (m, 2H); 3.10 (m, 2H); 2.75 (m, 2H); 2.46 (d, 2H, J=9 Hz); 2.32-2.05 (m, 3H); 2.00-1.68 (m, 9H); 0.90 (d, 6H, J=8 Hz).

According to the above described method and using the suitable amine as free base, the following compounds have been prepared:

2b (R,S) 2-(4-Isobutylphenyl)-N-Methyl-Propionamidine Hydrochloride from 2-(4-isobutylphenyl)propionitrile, prepared following the procedure described in Example 1, and the corresponding α-methylphenylacetamide.

Yield 75%. $^1$H-NMR (DMSO-d$_6$): δ 10.15 (bs, NH$^+$Cl$^-$); 7.12 (m, 4H); 4.25 (bs, NH$_2$); 3.71 (m, 1H); 2.90 (s, 3H); 2.48 (d, 2H, J=8 Hz); 1.91 (m, 1H); 1.55 (d, 3H, J=8 Hz); 0.93 (d, 6H, J=8 Hz).

2c (R,S) 2-(3-Benzoylphenyl)-N-[3-(N,N-Dimethylamino) Propyl]Propionamidine Hydrochloride From 2-(3-benzoylphenyl)propionitrile, prepared following the procedure described in Example 1, and the corresponding α-methylphenylacetamide.

Yield 48%. $^1$H-NMR (DMSO-d$_6$): δ 7.81 (d, 2H, J=8 Hz); 7.74 (s, 1H); 7.67 (d, 1H, J=8 Hz); 7.59 (d, 1H, J=8 Hz); 7.52-7.27 (m, 4H+NH); 3.65 (q, 1H, J=7 Hz); 3.25 (t, 2H, J=6 Hz); 2.27 (t, 2H, J=6 Hz); 2.09 (s, 6H); 1.66 (m, 2H); 1.46 (d, 6H, J=7 Hz).

Example 3

(R,S) 2-(4-Isobutylphenyl)Propionamidine Acetate Salt

As alternative procedure for the preparation of 2-(4-isobutylphenyl)propionamidines the method described in Judkins B. D., Allen D. G. Cook T. A., Evans B. and Sardharwala T. E., *Synth. Comm.*, 26(23), 4315-4367 (1996) has been followed:

(R,S) 2-(4-Isobutylphenyl)-N-Hydroxy-Propionamidine

A mixture of hydroxylamine hydrochloride (0.38 g, 5.32 mmol) and sodium tert-butoxide (0.5 g, 5.28 mmol) in ethyl alcohol (10 mL) is stirred at r.t. for 15'; the precipitate is filtered off and the mother liquors are added dropwise to a solution of 2-(4-isobutylphenyl)propionitrile (0.11 g, 0.49 mmol) in absolute ethyl alcohol (3 mL). The resulting solution is refluxed 18 h. After cooling at r.t. the solvents are evaporated under reduced pressure and the crude residue is diluted in trichloromethane (25 mL), washed with 5% solution of citric acid (2×15 mL), then with a saturated solution of NaCl (2×15 mL), dried over Na$_2$SO$_4$ and evaporated under vacuum to give 2-(4-isobutylphenyl)-N-hydroxy-propionamidine isolated as white solid after crystallisation from n-hexane (0.075 g, 0.34 mmol). Yield 70%. m.p. 75-78° C.

¹H-NMR (CDCl₃): δ 7.25 (d, 2H, J=7 Hz); 7.12 (d, 2H, J=7 Hz); 5.030 (bs, 1H, NH); 4.35 (bs, 2H, NH—OH); 3.58 (q, 1H, J=8 Hz); 2.48 (d, 2H, J=8 Hz); 1.87 (m, 1H); 1.50 (d, 3H, J=8 Hz); 0.92 (d, 6H, J=8 Hz).

2-(4-isobutylphenyl)-N-hydroxy-propionamidine (0.097 g, 0.44 mmol) is dissolved in acetic acid (3 mL) and treated at r.t. with acetic anhydride (0.06 mL, 0.66 mmol). 10% Pd on activated charcoal (0.03 g) is added and H₂ is bubbled into the flask until the complete disappearance of the starting reagent. Methyl alcohol (5 mL) is added, the catalyst filtered off on a Celite cake and the solvents evaporated under reduced pressure to give an oily residue. Crystallisation of the crude residue from n-hexane gives 2-(4-isobutylphenyl)propionamidine acetate salt as white solid (0.106 g, 0.4 mmol). Yield 91%. m.p. >220° C. ¹H-NMR (DMSO-d₆): δ 8.70-8.50 (bs, NH₃⁺+NH); 7.42 (d, 2H, J=7 Hz); 7.23 (d, 2H, J=7 Hz); 3.85 (q, 1H, J=8 Hz); 2.52 (d, 2H, J=8 Hz); 1.97 (m, 1H); 1.75 (s, 3H); 1.60 (d, 3H, J=8 Hz); 0.95 (d, 6H, J=8 Hz).

Example 4

The alternative method described in Weintraub L., Oles S. R. and Kalish N, *J. Org. Chem.*, 33(4), 1679-1681 (1968) has been followed for the preparation of 2-(4-isobutylphenyl)-N-alkyl-propionamidines.

4a (R,S) 2-(4-Isobutylphenyl)-N-[3-(N,N-Dimethylamino) Propyl]Propionamidine 4-isobutyl-α-methylphenylacetamide (1 g; 4.9 mmol), prepared according the procedure described in WO 00/24710, is dissolved in dry dichloromethane (10 mL) under inert atmosphere at r.t. and treated with triethyloxonium tetrafluoroborate (1.0 M in CH₂Cl₂, 5 mL, 5 mmol). The resulting solution is left stirring overnight at r.t. After solvent evaporation under reduced pressure, the crude intermediate is diluted in diethyl ether (5 mL) at r.t. and under inert CHCl₃/cyclohexane/CH₃OH/NH₄OH 60:24:17:2). The pure 2-(4-isobutylphenyl)-N-[3-(N,N-dimethylamino)propyl]propionamidine is obtained as pale yellow oil (0.82 g, 2.84 mmol). Yield 58%. ¹H-NMR (DMSO-d₆): δ 7.39 (d, 2H, J=8 Hz); 7.14 (d, 2H, J=8 Hz); 4.15 (q, 1H, J=7 Hz); 3.25 (t, 2H, J=7 Hz); 2.42 (d, 2H, J=7 Hz); 2.16 (t, 2H, J=7 Hz); 2.06 (s, 3H); 1.80 (m, 1H); 1.65 (m, 2H); 1.53 (d, 3H, J=7 Hz); 0.84 (d, 6H, J=7 Hz).

According to the above described method and using the N-benzylamine, the following compound has been prepared:

4b (R,S) 2-(4-Isobutylphenyl)-N-Benzyl Propionamidine

Yield 65%. ¹H-NMR (CDCl₃): δ 7.35-7.18 (m, 5H); 7.15 (d, 2H, J=8 Hz); 7.0.5 (d, 2H, J=8 Hz); 5.05 (bs, 2H, NH); 4.30 (s, 2H); 3.65 (q, 1H, J=7 Hz); 2.45 (d, 2H, J=7 Hz); 1.91 (m, 1H); 1.55 (d, 3H, J=7 Hz); 0.95 (d, 6H, J=7 Hz).

Example 5

(R,S) 3-[1-(4-Isobutylphenyl)Ethyl]-5,6-Dihydro-2H-1,2,4-Oxadiazine (R,S) 2-(4-isobutylphenyl)-N-hydroxy-propionamidine (50 mg, 0.23 mmol, preparation described in Example 3) is dissolved in 10 ml chloroform at room temperature. Excess sodium carbonate and 0.28 mmol 1,2-dichloroethane (28 mg; 20% excess) are added to this solution at r.t. The suspension is refluxed for 5 hours. After cooling, the inorganic salts are filtered off and the solution washed with brine (2×10 mL). The solvent is removed under reduced pressure and the title compound purified by column silica gel chromatography (n-hexane/ethyl acetate 9/1) to give 29 mg as a pale yellow oil (yield 51%)

¹H-NMR (CDCl13): δ 7.35 (d, 2H, J=7 Hz); 7.15 (d, 2H, J=7 Hz); 3.70 (q, 1H, J=8 Hz); 3.6-3.4 (m, 4H); 2.42 (d, 2H, J=8 Hz); 2,3-2.1 (m, 2H); 1.90 (m, 1H); 1.57 (d, 3H, J=8 Hz); 0.88 (d, 6H, J=8 Hz).

Example 6

(R,S) 2-[1-(4-Isobutylphenyl)Ethyl]-4,5-Dihydro-2H-1,3, Imidazole)

(R,S)-2-[(4-isobutyl)phenyl]-propionamidine hydrochloride (100 mg, 0.49 mmol, preparation described in Example 1a) were suspended in 25 mL dry chloroform at room temperature under inert atmosphere, then treated with a large excess (10-50 eq) of tButOK. To the suspension 0.59 mmol) 1,2-dichloroethane (58 mg; 20% excess) was added. The suspension was then refluxed for 24 hour. At room temperature the suspended solid was filtered and the solution washed with 5% phosphate buffer pH 5 and brine. The solution dried over sodium sulphate was evaporated; the residue oil was chromatographed on silica gel column to obtain the pure title compound (73 mg; 65% Yield).

¹H-NMR (CDCl3): δ 7.40 (d, 2H, J=7 Hz); 7.15 (d, 2H, J=7 Hz); 3.75 (q, 1H, J=8 Hz); 3.5-3.6 (m, 4H); 2.42 (d, 2H, J=8 Hz); 1.90 (m, 1H); 1.57 (d, 3H, J=8 Hz); 0.88 (d, 6H, J=8 Hz).

The chemical structure of the compounds of examples 1-6 is reported in table 1.

TABLE 1

| Example N. | Chemical name | Structure Formula |
|---|---|---|
| 1a | (R,S) 2-(4-isobutylphenyl)-propionamidine hydrochloride | 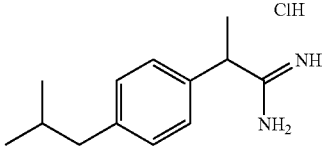 |
| 1b | (R,S) 2-(3-benzoylphenyl)propionamidine hydrochloride | 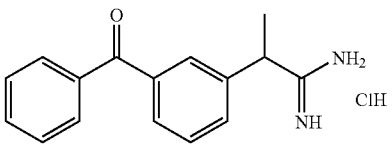 |

TABLE 1-continued

| Example N. | Chemical name | Structure Formula |
|---|---|---|
| 1c | (R,S) 2-(3-fluoro-4-phenyl)phenylpropionamidine hydrochloride | |
| 1d | (R,S) 2-(4-trifluoromethanesulphonyloxy) phenylpropionamidine hydrochloride | |
| 1e | (R,S) 2-(5-benzoyl-2-thiophene)propionamidine hydrochloride | |
| 2a | (R,S) 2-[(4-isobutyl)phenyl]-N-[3-N-piperidinopropyl] propionamidine dihydrochloride | |
| 2b | (R,S) 2-[(4-isobutyl)phenyl]-N-methyl-propionamidine | |
| 2c | (R,S) N-[(3-(N,N-dimethylamino)-propyl]-2-(3-benzoylphenyl)propionamidine | |
| 3 | (R,S) 2-(4-isobutylphenyl)-propionamidine acetate | |
| 4a | (R,S) 2-(4-isobutylphenyl)-N-(3-dimethylaminopropyl)-propionamidine | |

TABLE 1-continued

| Example N. | Chemical name | Structure Formula |
|---|---|---|
| 4b | (R,S) 2-(4-isobutylphenyl)-N-benzyl propionamidine | |
| 5 | (R,S) 3-[1-(4-isobutylphenyl)ethyl]-5,6-dihydro-2H-1,2,4-oxadiazine | |
| 6 | (R,S) 2-[1-(4-isobutylphenyl)ethyl]-4,5-dihydro-2H-1,3,imidazole) | |

What is claimed is:

1. Amidines of formula (I)

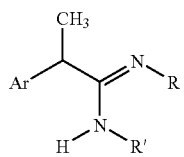

and pharmaceutically acceptable salts thereof,
wherein Ar is selected from:
  3'-benzoylphenyl, 3'-(4-chloro-benzoyl)-phenyl, 3'-(4-methyl-benzoyl)-phenyl,
  3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl,
  4'-benzenesulfonylamino-phenyl, 4'-benzenesulfonylmethyl-phenyl, 4'-acetoxyphenyl,
  4'-propionyloxy-phenyl, 4'-benzoyloxy-phenyl, 4'acetylamino-phenyl, 4'propionylamino-phenyl, 4'-benzoylamino-phenyl;
R' is selected from
  H, $C_1$-$C_5$-alkyl, phenyl, $C_1$-$C_5$-phenyalkyl, $C_1$-$C_5$-cycloalkyl, $C_1$-$C_5$-alkenyl, $C_1$-$C_5$-alkoxy;
  a residue of formula —(CH$_2$)n-NRaRb wherein n is an integer from 0 to 5 and each Ra and Rb, which may be the same or different, are $C_1$-$C_6$-alkyl, $C_1$-$C_6$-alkenyl or, alternatively, Ra and Rb, together with the nitrogen atom to which they are bound, form a heterocycle from 3 to 7 members of formula (II),

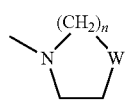

wherein W represents a single bond, O, S, N-Rc, Rc being H, $C_1$-$C_6$-alkyl or $C_1$-$C_6$-alkylphenyl, n is an integer from 0 to 4"
R is H, $CH_3$, $CH_2CH_3$.

2. The compound according to claim 1, wherein R' is selected from
hydrogen
a residue of formula —(CH$_2$)$_n$-NRaRb, wherein n is an integer 2 or 3 and the group NRaRb is selected from N,N-dimethylamine or 1-piperidyl, and R is H.

3. The compound according to claim 1 selected from:
(+) (2-(4-isobutylphenyl)propionamidine hydrochloride
(−) (2-(4-isobutylphenyl)propionamidine hydrochloride
(R,S) 2-(3-benzoylphenyl)propionamidine hydrochloride
(R,S) 2-(3-benzoylphenyl)propionamidine hydrochloride
(R,S) 2-[(3-fluoro-4-phenyl)phenyl]propionamidine hydrochloride
(R,S) 2-(5-benzoyl-2-thiophene)propionamidine hydrochloride
(R,S) 2-(4-isobutylphenyl)-N-[3"-(N'-piperidino)propyl] propionamidine dihydrochloride
(R,S) 2-(4-isobutylphenyl)-N-methyl-propionamidine hydrochloride
(R,S) 2-(3-benzoylphenyl)-N-[3-(N,N-dimethylamino) propyl]propionamidine hydrochloride
(R,S) 2-(4-isobutylphenyl)propionamidine acetate salt
(R,S) 2-(4-isobutylphenyl)-N-[3-(N,N-dimethylamino) propyl]propionamidine, and
(R,S) 2-(4-isobutylphenyl)-N-benzyl propionamidine.

4. A process for the preparation of compounds of formula (I)

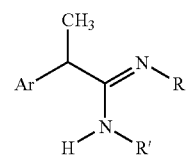

and pharmaceutically acceptable salts thereof, wherein Ar is selected from:
3'-benzoylphenyl, 3'-(4-chloro-benzoyl)-phenyl, 3'-(4-methyl-benzoyl)-phenyl,
3'-acetyl-phenyl, 3'-propionyl-phenyl, 3'-isobutanoyl-phenyl, 4'-trifluoromethanesulfonyloxy-phenyl, 4'-benzenesulfonyloxy-phenyl, 4'-trifluoromethanesulfonylamino-phenyl, 4'-benzenesulfonylamino-phenyl, 4'-benzenesulfonylmethyl-phenyl, 4'-acetoxyphenyl, 4'-propionyloxy-phenyl, 4'-benzoyloxy-phenyl, 4'acetylamino-phenyl, 4'propionylamino-phenyl, 4'-benzoylamino-phenyl;

R' is selected from
  H, $C_1$-$C_5$-alkyl, phenyl, $C_1$-$C_5$-phenyalkyl, $C_1$-$C_5$-cycloalkyl, $C_1$-$C_5$-alkenyl, $C_1$-$C_5$-alkoxy;
  a residue of formula —$(CH_2)_n$-NRaRb wherein n is an integer from 0 to 5 and each Ra and Rb, which may be the same or different, are $C_1$-$C_6$-alkyl, $C_1$-$C_6$-alkenyl or, alternatively, Ra and Rb, together with the nitrogen atom to which they are bound, form a heterocycle from 3 to 7 members of formula (II),

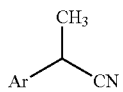
(II)

wherein W represents a single bond, O, S, N-Rc, Rc being H, $C_1$-$C_6$-alkyl or $C_1$-$C_6$-alkylphenyl, n is an integer from 0 to 4"
R is H, $CH_3$, $CH_2CH_3$;
comprising reacting a nitrile derivative of formula (IV),

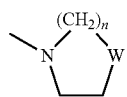
(IV)

wherein Ar is a phenyl group non-substituted or substituted by one or more groups independently selected from halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halogen-$C_1$-$C_3$-alkyl, halogen $C_1$-$C_3$-alkoxy, benzoyl or a substituted or unsubstituted 5-6 membered heteroaryl ring selected from pyridine, pyrrole, thiophene, furane, and indole, with an amine of formula NHR, wherein R is selected from the group consisting of: —H, $C_1$-$C_5$-alkyl, phenyl, $C_1$-$C_5$-phenyalkyl, $C_1$-$C_5$-cycloalkyl, $C_1$-$C_5$-alkenyl, $C_1$-$C_5$-alkoxy; and residues of formula —$(CH_2)$n-NRaRb, wherein n is an integer from 1 to 5 and Ra and Rb are independently $C_1$-$C_6$-alkyl, $C_1$-$C_6$-alkenyl or Ra and Rb, together with the nitrogen atom to which they are bound, form a heterocycle from 3 to 7 members of formula (II),

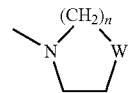
(II)

wherein W represents a single bond, O, S, N-Rc, Rc being H, $C_1$-$C_6$-alkyl or $C_1$-$C_6$-alkylphenyl.

5. Pharmaceutical compositions comprising a compound according to claim 1 in admixture with a suitable carrier thereof.

6. A method for treatment of psoriasis, ulcerative colitis, melanoma, chronic obstructive pulmonary disease (COPD), bullous pemphigo, rheumatoid arthritis, idiopathic fibrosis, glomerulonephritis, or for the treatment of damage caused by ischemia and reperfusion comprising administering the composition of claim 5 to a patient in need thereof.

7. A method for inhibiting in vitro IL-8-induced chemotaxis of human polymorphonuclear cells, comprising contacting said cells with a compound of claim 1.

\* \* \* \* \*